United States Patent [19]

Wagner et al.

[11] 4,178,385

[45] Dec. 11, 1979

[54] METHOD FOR TREATING HYPERLIPIDEMIA IN PRIMATES USING 4-((4-FLUOROPHENYLMETHYL)AMINO)-BENZOIC ACID

[75] Inventors: Eugene R. Wagner, Carmel; Alfred A. Renzi, Zionsville, both of Ind.

[73] Assignee: The Dow Chemical Company, Midland, Mich.

[21] Appl. No.: 883,091

[22] Filed: Mar. 3, 1978

[51] Int. Cl.$^2$ ............... A61K 31/195; A61K 31/205; A61K 31/24

[52] U.S. Cl. ................ 424/310; 260/448 R; 260/501.11; 424/287; 424/316; 424/319; 560/47; 562/456

[58] Field of Search ............ 424/310, 319, 287, 316; 560/47; 260/448 R, 501.11, 518 A; 562/456

[56] References Cited

U.S. PATENT DOCUMENTS 3,868,416  2/1975  Albright et al. ............... 260/518 R

FOREIGN PATENT DOCUMENTS 7602332  9/1976  Netherlands.

OTHER PUBLICATIONS

Aumüller et al., Chemical Abstracts, vol. 48 (1954) 6496.

Primary Examiner—Richard Raymond

[57] ABSTRACT

A method for treating hyperlipidemia in primates using the compound 4-((4-fluorophenylmethyl)amino)benzoic acid, a pharmaceutically-acceptable salt or an ester thereof.

5 Claims, No Drawings

METHOD FOR TREATING HYPERLIPIDEMIA IN PRIMATES USING 4-((4-FLUOROPHENYLMETHYL)AMINO)BENZOIC ACID

BACKGROUND OF THE INVENTION

As established by various studies, it is recognized that cholesterol and triglycerides play a major role in the formation of arteriosclerotic plaques by accelerating the deposition of blood lipids in the arterial wall.

Various para(aryl(alkyl)amino)benzoic acids, esters, and salts thereof have been described as useful in lowering the serum lipid levels in mammals. See Dutch Patent Application No. 7,602,332 filed Sept. 14, 1976. Although this publication describes a number of substituted and unsubstituted benzylamino benzoic acids which may be used to lower the serum lipid levels in rodents, these compounds are not necessarily useful in lowering lipid levels in primates. Hypolipidemic activity in primates cannot be predicted from data collected in rats. Therefore compounds found to be highly active in the rat are not necessarily of use in lowering serum lipid levels in a primate. For example, the compounds 4-((4-chlorophenylmethyl)amino)benzoic acid and 4-((2-fluorophenylmethyl)amino)benzoic acid are known to be active hypolipidemic agents in rats, but neither compound shows activity in primates.

SUMMARY OF THE INVENTION

The present invention is directed to a method for lowering serum lipid levels in a primate which comprises administering internally to the primate a hypolipidemically effective amount of the compound 4-((4- -fluorophenylmethyl)amino)benzoic acid, a pharmaceutically-acceptable salt, or a lower ester thereof. As used in the specification and claims, the term "lower ester" refers to an ester of the subject compound wherein the alkyl moiety contains from one to about three carbon atoms, the ethyl ester generally being preferred.

Pharmaceutically-acceptable salts of 4-((4- -fluorophenylmethyl)amino)benzoic acid are considered as being within the scope of this invention. Pharmaceutically-acceptable salts refer to the acid addition salts of those bases which will form a salt with a carboxylic acid and which will not cause an adverse physiological effect when administered to an animal at dosages consistent with good pharmacological activity. Suitable bases thus include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary, and tertiary amines and the like. Also aluminum salts of the instant compounds may be obtained by treating the corresponding sodium salt with an appropriate aluminum complex such as aluminum chloride hexahydrate, etc.

As noted above, the subject compound, the pharmaceutically-acceptable salts, and the lower esters thereof have shown hypolipidemic activity in primates, that is an animal belonging to the taxonomic order Primata. Hypolipidemic activity as used herein refers to the effect of lowering the blood lipid content and in particular the cholesterol and triglyceride content of the serum. The compounds of the present invention are therefore suitable for use in treating serum hyperlipidemia in primates and in particular are useful for the treatment of hypercholesterolemia and hypotriglyceridemia, that is, abnormally high levels of lipids, cholesterol, or triglycerides, respectively, in the serum. The compounds can be administered orally or parenterally by subcutaneous, intravenous, or intraperitoneal injection or by implantation or the like, oral administration being preferred.

The hypolipidemic amount of the p-benzylaminobenzoic acid compounds to be administered to a primate, that is, the amount which is effective to significantly lower the serum lipid level, can vary depending upon such factors as the particular animal treated, the particular p-benzylaminobenzoic acid compound employed, the desired lipid level to be obtained, whether or not the primate is hyperlipidemic, the period of administration and the method of administration. In general an effective daily dosage range is from about 1 to 400 milligrams per kilogram of body weight, with a daily dosage range of from about 5 to about 15 mg/kg of body weight being preferred.

For oral administration, pharmaceutical preparations of the p-amino benzoic acids may be made by following the conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linguets, powders, capsules, slurries, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, disintegrating agents such as maize starch or alginic acid, and lubricating agents such as magnesium stearate may be used.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically-acceptable oils as carriers. For example vegetable or animal oils such as sunflower oil, safflower oil, maize oil or cod liver oil can be used. Glycerine can also be used. With this latter solvent, from 2 to 30 percent water may be added. When water alone is the carrier, or when the solubility of the compound in the oil is low, the preparations can be administered in the form of a slurry.

Emulsion compositions may be formulated using emulsifying agents such as sorbitan trioleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example a hydrophilic colloid such as polyvinylpyrrolidone. The emulsions and suspensions may contain conventional excipients such as sweeting agents, flowing agents, coloring materials and preservatives.

The p-amino benzoic acids can also be incorporated in a nutritive foodstuff such as, for example, butter, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged asceptically. They may be administered intravenously or intramuscularly. Useful solvents for formulation in such use are the polyhydric aliphatic alcohols and mixtures thereof. Especially satisfactory are the pharmaceutically-acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly convenient solvent system. A ph range, about 7.4, and isotonicity comparible with body isotonicity, is desirable. Basicity may be controlled by addition of a base as required, and a particularly convenient base is monoethanolamine. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

DETAILED DESCRIPTION OF THE INVENTION

The compound 4-((4-fluorophenylmethyl)amino)benzoic acid is prepared by known procedures. In one method, the subject compound is prepared by reacting p-aminobenzoic acid in an inert solvent with 4-fluorobenzaldehyde. The resulting Schiff base may be reduced to prepare the corresponding subject compound. A convenient method of carrying out this latter procedure involves mixing about 0.1 mol. of the Schiff base with an excess of ethanol and water. Dilute aqueous sodium hydroxide, for example about 0.1 molar equivalent of the Schiff base, optionally can be added to the mixture. Sodium borohydride, $NaBH_4$, (0.1 mol.) is added at room temperature and stirred until it dissolves. The mixture is then heated to reflux for 1 to 2 hours. The mixture is poured onto ice and acidified. The product may be filtered off as a precipitate and further purified by known procedures as required.

The hypolipidemic effect of 4-((4-fluorophenylmethyl)amino)benzoic acid was followed in a male and female cynomalgus monkey (*Macaca fasicularis*). Daily oral doses of 200 mg/kg of body weight were administered by nasogastric intubation during the first two weeks of the study. The dosage was increased weekly during the remaining four weeks of the test period. The results are shown in Table I.

TABLE I

| Animal | Dosage mg/kg/day | Time Period | Serum Cholesterol mg/dl | Percent Change | Serum Triglycerides mg/dl | Percent Change |
|---|---|---|---|---|---|---|
| Male | None | Control | 152 | | 44 | |
| " | None | Control | 161 | | 20 | |
| " | 200 | 1st week | 121 | −20.4 | 17 | −47 |
| " | 200 | 2nd week | 120 | −23.5 | 18 | −44 |
| " | 300 | 3rd week | 128 | −18.4 | 22 | −31 |
| " | 400 | 4th week | 104 | −33.7 | 28 | −13 |
| " | 500 | 5th week | 99 | −37.0 | 37 | +16 |
| " | 600 | 6th week | 104 | −33.7 | 16 | −50 |
| Female | None | Control | 173 | | 68 | |
| " | None | Control | 179 | | 64 | |
| " | 200 | 1st week | 152 | −13.6 | 76 | +13.2 |
| " | 200 | 2nd week | 156 | −11.3 | 54 | −18 |
| " | 300 | 3rd week | 173 | −2.0 | 57 | −14 |
| " | 400 | 4th week | 157 | −11.0 | 86 | +30 |
| " | 500 | 5th week | 131 | −25.5 | 99 | +50 |
| " | 600 | 6th week | 134 | −23.8 | 69 | +5 |

The data in Table I indicate that the subject compound will significantly reduce serum cholesterol in monkeys when used in accordance with the method of the present invention. Although the female monkey showed some significant increases in serum triglyceride levels during part of the test period, looking at the data from both animals indicates an overall decrease in serum triglycerides.

We claim:

1. A method for lowering serum lipid levels in a primate which comprises administering internally to the primate an effective hypolipidemic amount of the compound 4-((4-fluorophenylmethyl)amino)benzoic acid, a pharmaceutically-acceptable salt or a lower ester thereof.

2. The method of claim 1 wherein the compound is 4-((4-fluorophenylmethyl)amino)benzoic acid.

3. The method of claim 1 wherein the compound is a salt.

4. The method of claim 3 wherein the salt is a hydrochloride salt.

5. The method of claim 1 wherein the compound is the ethyl ester of 4-((4-fluorophenylmethyl)amino)benzoic acid.

* * * * *